United States Patent [19]

Massaroli

[11] Patent Number: 4,769,374

[45] Date of Patent: Sep. 6, 1988

[54] TETRAHYDROISOQUINOLINE ETHYL ESTERS OF 1,4-DIHYDROPYRIDINES AND ANTIHYPERTENSIVE COMPOSITIONS

[75] Inventor: Giangiacomo Massaroli, Rovagnate, Italy

[73] Assignee: Poli Industria Chimica S.p.A., Milan, Italy

[21] Appl. No.: 779,243

[22] Filed: Sep. 23, 1985

[30] Foreign Application Priority Data

Sep. 28, 1984 [IT] Italy ................................ 22898 A/84

[51] Int. Cl.$^4$ ..................... A61K 31/47; C07D 401/12
[52] U.S. Cl. ..................................... 514/307; 546/147
[58] Field of Search ................. 546/147, 321; 514/307

[56] References Cited

U.S. PATENT DOCUMENTS 3,996,234 12/1976 Bossert et al. ........................ 546/321
4,652,573 3/1987 Minaskanian et al. ............... 546/187

*Primary Examiner*—Mary C. Lee
*Assistant Examiner*—Dale A. Bjorkman
*Attorney, Agent, or Firm*—Bucknam and Archer

[57] ABSTRACT

1,4-Dihydropiridine derivatives having the formula

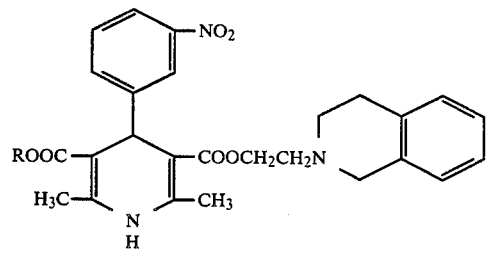

(I)

wherein R is methyl, ethyl or isopropyl, are endowed with a hypotensive, vasodilator and Ca$^{++}$-antagonistic activity.

7 Claims, No Drawings

TETRAHYDROISOQUINOLINE ETHYL ESTERS OF 1,4-DIHYDROPYRIDINES AND ANTIHYPERTENSIVE COMPOSITIONS

The present invention relates to 1,4-dihydropyridine derivatives of general formula I

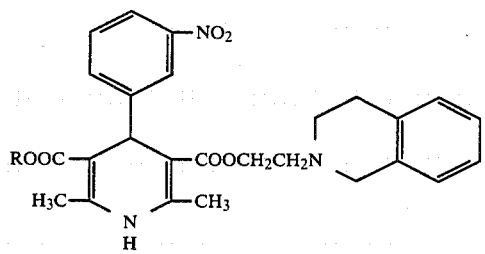

wherein R is methyl, ethyl or iospropyl, and to addition salts thereof with pharmaceutically acceptable acids.

The compounds according to the invention show an in vitro $Ca^{++}$-antagonistic activity which is comparable to the activity exhibited by Nifedipine and Nicardipine, i.e. two well-known calcium antagonistic drugs (U.S. Pat. Nos. 3,485,847, 3,644,627 and, respectively, Japan Kokai 74 109384).

Furthermore, the compounds according to the invention show a high and long lasting hypotensive activity, whose duration is superior to the Nifedipine's one and comparable to the Nicardipine's one, being at the same time much less toxic than these two drugs. Therefore, in comparison with Nifedipine and Nicardipine, the compounds according to the invention exhibit a better therapeutic index as drugs endowed with coronaric and peripheral vasodilating, hypotensive and antianginous activity.

Therefore, another object of the present invention consists in pharmaceutical compositions with vasodilating, hypotensive and antianginous activity, containing as the active component one or more of the compounds according to the invention.

The compounds of formula I may be prepared, according to a per se known process, by reacting substantially equimolecular quantities of an alkyl 3-aminocrotonate ($CH_3$—$C(NH_2)$=$CH$—$COOR$, wherein R is as above defined), 3-nitrobenzaldehyde and 2-(1,2,3,4-tetrahydro-isoquinoline-2-yl)ethyl acetoacetate, in an alcoholic boiling medium, according to the following scheme:

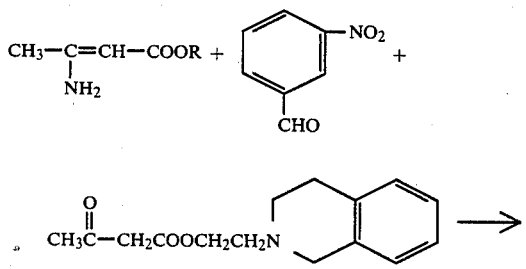

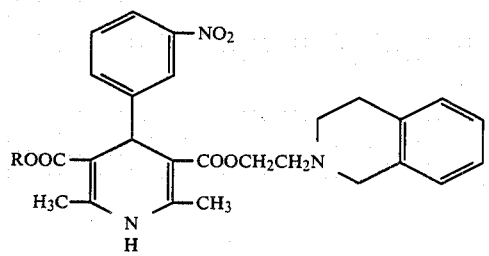

The following example is submitted by way of illustration of the invention.

EXAMPLE 2-(1,2,3,4-Tetrahydro-isoquinoline-2-yl)ethyl 1,4-dihydro-2,6-dimethyl-4-(3-nitrophenyl)-5-methoxycarbonyl-pyridine-3-carboxylate, mono-hydrochloride (I, R=$CH_3$)

A mixture of 13.05 g (0.05 mol) of 2-(1,2,3,4-tetrahydroisoquinoline-2-yl)ethyl acetoacetate, 5.75 g (0.05 mol) of methyl 3-aminocrotonate and 7.55 g (0.05 mol) of 3-nitrobenzaldehyde in 40 ml of isopropanol was refluxed for 7 hours. The solvent was evaporated in vacuo and the residue was dissolved in 20 ml of ethyl acetate and purified through chromatography on $Al_2O_3$, eluting with ethyl acetate. The fractions containing the title product were collected, evaporated to dryness in vacuo, and the oily residue was dissolved in 70 ml of chloroform. The resulting solution was shaken with 30 ml of an aqueous solution of 2N HCl, the organic layer was separated, dried over sodium sulfate and dried under vacuum. The obtained residue was crystallized from ethanol, thus giving a yellowish crystalline product melting at 210°–212° C.

Yield 12.4 g (47% of theoretical).

Elemental analysis for $C_{27}H_{29}N_3O_6.HCl$

|  | C | H | N |
|---|---|---|---|
| Calc. % | 61.41 | 5.53 | 7.95 |
| Found % | 61.29 | 5.64 | 7.86 |

The following compounds of formula I were prepared by operating substantially as in the foregoing example: R=$C_2H_5$; m.p. 192°–194° (EtOH).

Elemental analysis for $C_{28}H_{31}N_3O_6.HCl$

|  | C | H | N |
|---|---|---|---|
| Calc. % | 62.04 | 5.76 | 7.75 |
| Found % | 61.88 | 5.71 | 7.56 |

R=$CH(CH_3)_2$; m.p. 169°–171° (EtOH—$Et_2O$). Elemental analysis for $C_{29}H_{33}N_3O_6.HCl$

|  | C | H | N |
|---|---|---|---|
| Calc. % | 62.64 | 5.98 | 7.55 |
| Found % | 62.70 | 5.92 | 7.43. |

The pharmaco-toxicological properties of the compounds of the invention will hereinbelow be described.

Ca++ antagonistic activity

The in vitro Ca++ antagonistic activity, determined on helicoidal segments of thoracic aorta of rats, according to T. Godfraind in J. Pharm. Exptl. Ther. 224; 443 (1983), was expressed as $IC_{50}$ (concentration reducing of 50% the contraction induced by $CaCl_2$).

The results are reported in the following Table 1.

TABLE 1

Ca++ antagonistic activity on the isolated rat aorta stimulated by $CaCl_2$

| Compound | $IC_{50}$ (mg/ml) |
| --- | --- |
| I, R = $CH_3$ | 2.4 |
| I, R = $C_2H_5$ | 2.7 |
| I, R = $CH(CH_3)_2$ | 3.1 |
| Nifedipine | 2.8 |
| Nifedipine | 2.5 |

Antihypertensive activity

The antihypertensive activity was determined by administering spontaneous hypertensive rats with the compounds of the invention, by oral route, as a suspension in carboxymethylcellulose containing 0.5% of physiologic solution. The systolic pressure of the caudal artery was recorded after 15 minutes, 1 hour, 3 hours and 5 hours after the administration of the compound to be tested. The obtained results are reported in Table 2, and are expressed as the percentage of the decrease of the sistolic pressure after treatment.

TABLE 2

Antihypertensive activity per os

| Compound | Dose mg/kg | Number of animals | Pressure (mm Hg) Time 0 | Pressure variations (pressure time 0 - less pressure after administration) | | | |
| --- | --- | --- | --- | --- | --- | --- | --- |
| | | | | 15 min. | 1 h | 3 h | 5 h |
| I, R = $CH_3$ | 3 | 5 | 185 ± 6.4 | 54 ± 6.4 | 86 ± 7.3 | 73 ± 12.8 | 49 ± 8.7 |
| I, R = $C_2H_5$ | 3 | 5 | 207 ± 10.2 | 43 ± 10.2 | 31 ± 7.1 | 22 ± 9.4 | 11 ± 6.9 |
| I, R = $CH(CH_3)_2$ | 3 | 5 | 192 ± 8.2 | 39 ± 7.6 | 38 ± 6.9 | 18 ± 6.1 | 2 ± 3.1 |
| Nifedipine | 3 | 5 | 184 ± 8.3 | 41 ± 5.4 | 23 ± 6.1 | 12 ± 4.3 | 9 ± 5.6 |
| Nicardipine | 3 | 5 | 188 ± 4.6 | 49 ± 11.3 | 52 ± 9.7 | 36 ± 6.2 | 21 ± 5.8 |

Acute toxicity

The acute toxicity was determined on mice of both sexes upon oral administration of the compounds to be tested as a suspension in carboxymethylcellulose containing 0.5% of physiologic solution, and it was expressed as an $LD_{50}$ value at day 14 of observation. The obtained results are reported in Table 3.

TABLE 3

Acute toxicity in mice

| Compound | $LD_{50}$ p.o. mg/kg |
| --- | --- |
| I, R = $CH_3$ | 1,000 |
| I, R = $C_2H_5$ | 1,000 |
| I, R = $CH(CH_3)_2$ | 1,000 |
| Nifedipine | 750 |
| Nicardipine | 350 |

The present invention also refers to all of the industrially applicable aspects connected with the use of the compounds of the invention as antihypertensive, antianginous, coronary and peripheral vasodilating agents. Therefore, an essential aspect of the invention is represented by pharmaceutical compositions containing at least a compound of the invention, alone or in admixture with a pharmaceutical carrier, in the form of tablets, sugar coated tablets, capsules, powders, granules for oral solutions or suspensions, syrups.

The active ingredients may be alone or in the form of capsules. Alternatively, they can be formulated by using common pharmaceutical carriers, such as, for instance, lactose or talc, granulating agents like magnesium stearate or stearic acid, suspending agents like methylcellulose and/or surfactants like the polyoxyethylene stearates; preserving agents, e.g. ethyl p-hydroxybenzoate, as well as flavoring agents. Preferably, the pharmaceutical compositions according to the present invention are in unit dosage forms containing from 10 to 500 mg of the compounds of formula I in admixture with a pharmaceutical carrier. These unit dosage forms can be administered from one to three times per day.

I claim:

1. A compound of formula I

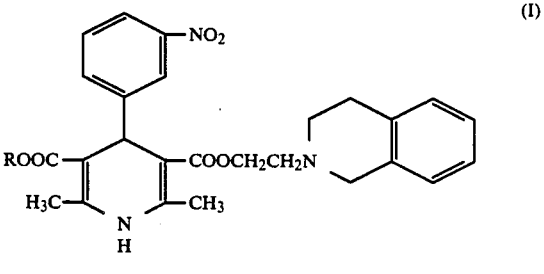

(I)

wherein R is a member selected from the group consisting of methyl, ethyl, isopropyl, and salts thereof with a pharmaceutically acceptable acid.

2. A compound as defined in claim 1, which is 2(1,2,3,4-tetrahydro-isoquinoline-2-yl)ethyl 1,4-dihydro-2,6-dimethyl-4-(3-nitrophenyl)-5-methoxycarbonyl-pyridine-3-carboxylate, mono-hydrochloride.

3. A compound as defined in claim 1, which is 2-(1,2,3,4-tetrahydro-isoquinoline-2-yl)ethyl 1,4-dihydro-2,6-diethyl-4-(3-nitrophenyl)-5-ethoxycarbonyl-pyridine-3-carboxylate, mono-hydrochloride.

4. A compound as defined in claim 1, which is 2-(1,2,3,4-tetrahydro-isoquinoline-2-yl)ethyl 1,4-dihydro-2,6-diisopropyl-4-(3-nitrophenyl)-5-isopropoxycarbonyl-pyridine-3-carboxylate, mono-hydrochloride.

5. A pharmaceutical composition with antihypertensive, antianginous, coronary and peripheral vasodilating activity containing, as the active ingredient, at least one compound of formula I

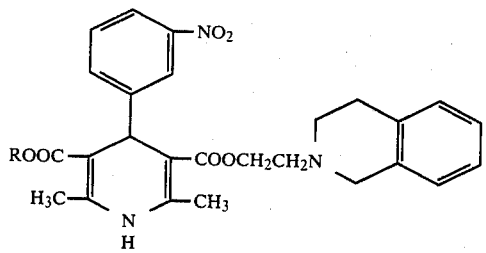

(I)

wherein R is a member selected from the group consisting of methyl, ethyl, isopropyl, and salts thereof with a pharmaceutically acceptable acid and a pharmaceutical carrier.

6. Pharmaceutical compositions according to claim 5, suitable for oral administrations.

7. The composition according to claim 5 in unit dosage form containing 10–500 mgs. of said compound of formula I per dose.

* * * * *